United States Patent
Kim et al.

(10) Patent No.: US 11,801,276 B2
(45) Date of Patent: Oct. 31, 2023

(54) MICROORGANISM HAVING ABILITY TO DEGRADE ETHANOL AND ACETALDEHYDE, AND COMPOSITION AND KIT EACH INCLUDING THE SAME

(71) Applicant: Medytox Inc., Cheongju-si (KR)

(72) Inventors: Young In Kim, Seongnam-si (KR); Tai Hoon Kim, Gimpo-si (KR); Hyei Jin Dong, Suwon-si (KR); Woo Jin Choi, Suwon-si (KR); Hyun Uk Jeong, Suwon-si (KR); Seong Gon Hong, Gimpo-si (KR); Dong Wook Ryu, Anyang-si (KR)

(73) Assignee: Medytox Inc., Cheongju-si (KR)

( * ) Notice: Subject to any disclaimer, the term of this patent is extended or adjusted under 35 U.S.C. 154(b) by 552 days.

(21) Appl. No.: 16/959,072

(22) PCT Filed: Nov. 8, 2018

(86) PCT No.: PCT/KR2018/013522
§ 371 (c)(1),
(2) Date: Jun. 29, 2020

(87) PCT Pub. No.: WO2019/132233
PCT Pub. Date: Jul. 4, 2019

(65) Prior Publication Data
US 2020/0330532 A1    Oct. 22, 2020

(30) Foreign Application Priority Data

Dec. 29, 2017  (KR) .................. 10-2017-0184821

(51) Int. Cl.
| | | |
|---|---|---|
| A61K 35/747 | (2015.01) | |
| A23L 33/135 | (2016.01) | |
| A23C 9/12 | (2006.01) | |
| A23C 9/123 | (2006.01) | |
| C12N 1/20 | (2006.01) | |
| A23C 15/12 | (2006.01) | |

(52) U.S. Cl.
CPC .............. *A61K 35/747* (2013.01); *A23C 9/12* (2013.01); *A23C 9/1234* (2013.01); *A23C 15/12* (2013.01); *A23L 33/135* (2016.08); *C12N 1/20* (2013.01); *C12N 1/205* (2021.05); *A23Y 2220/13* (2013.01); *A23Y 2220/35* (2013.01)

(58) Field of Classification Search
None
See application file for complete search history.

(56) References Cited

U.S. PATENT DOCUMENTS

| | | | |
|---|---|---|---|
| 6,037,158 A | | 3/2000 | Hummel et al. |
| 2006/0233774 A1 * | | 10/2006 | Lim ...................... A23L 33/105 424/769 |

FOREIGN PATENT DOCUMENTS

| | | | |
|---|---|---|---|
| KR | 1020050042860 A | 5/2005 | |
| KR | 1020060059588 A | 6/2006 | |
| KR | 1020060065753 A | 6/2006 | |
| KR | 1020130092182 A | 8/2013 | |
| KR | 1020130092183 A | 8/2013 | |
| KR | 1670048 B1 * | 10/2016 | ........... A23L 33/135 |
| KR | 101880650 B1 | 7/2018 | |
| KR | 101880651 B1 | 7/2018 | |

OTHER PUBLICATIONS

Japanese Office Action dated Aug. 17, 2021, issued in Japanese Application No. 2020-536122 (with English translation).
Written Opinion and International Search Report dated Feb. 11, 2019, issued in International Application No. PCT/KR2018/013522.

* cited by examiner

*Primary Examiner* — Michelle F. Paguio Frising
(74) *Attorney, Agent, or Firm* — Potomac Law Group, PLLC

(57) ABSTRACT

Provided are a microorganism having an ability to degrade ethanol and acetaldehyde, and a composition and a kit each including the microorganism.

10 Claims, 1 Drawing Sheet

Specification includes a Sequence Listing.

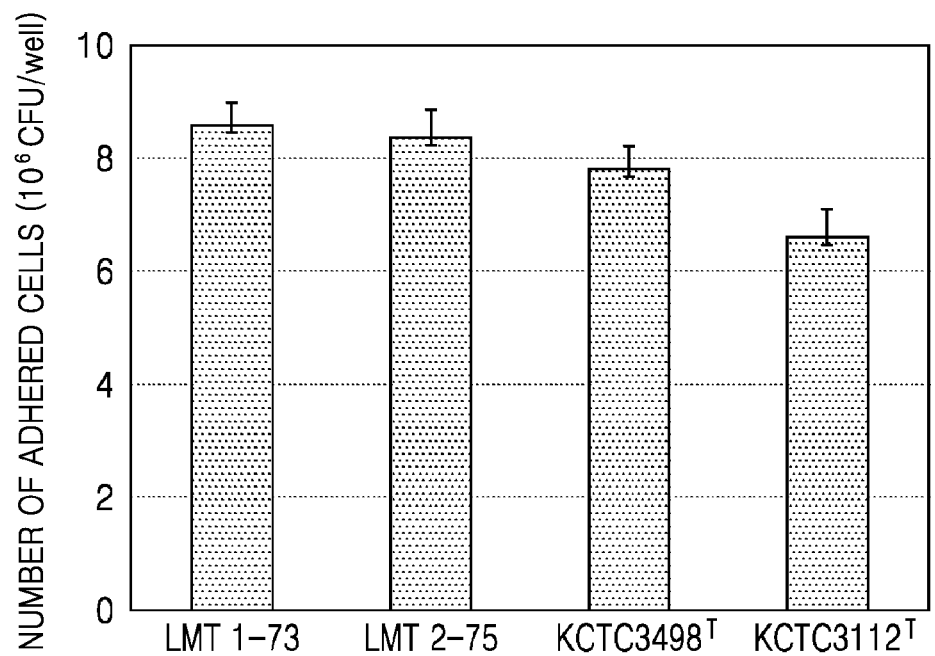

SEQUENCE LISTING

<160> NUMBER OF SEQ ID NOS: 16

<210> SEQ ID NO 1
<211> LENGTH: 1369
<212> TYPE: DNA
<213> ORGANISM: Lactobacillus brevis

<400> SEQUENCE: 1

```
ttgcactgat ttcaacaatg aagcgagtgg cgaactggtg agtaacacgt gggaaatctg      60
cccagaagca ggggataaca cttggaaaca ggtgctaata ccgtataaca acaaaatccg     120
catggatttt gtttgaaagg tggcttcggc tatcacttct ggatgatccc gcggcgtatt     180
agttagttgg tgaggtaaag gcccaccaag acgatgatac gtagccaacc tgagagggta     240
atcggccaca ttgggactga gacacggccc aaactcctac gggaggcagc agtagggaat     300
cttccacaat ggacgaaagt ctgatggagc aatgccgcgt gagtgaagaa gggtttcggc     360
tcgtaaaact ctgttgttaa agaagaacac ctttgagagt aactgttcaa gggttgacgg     420
tatttaacca gaaagccacg gctaactacg tgccagcagc cgcggtaata cgtaggtggc     480
aagcgttgtc cggatttatt gggcgtaaag cgagcgcagg cggttttttta agtctgatgt     540 gaaagccttc ggcttaaccg gagaagtgca tcggaaactg ggagacttga gtgcagaaga     600
ggacagtgga actccatgtg tagcggtgga atgcgtagat atatggaaga acaccagtgg     660
cgaaggcggc tgtctagtct gtaactgacg ctgaggctcg aaagcatggg tagcgaacag     720
gattagatac cctggtagtc catgccgtaa acgatgagtg ctaagtgttg gagggtttcc     780
gcccttcagt gctgcagcta acgcattaag cactccgcct ggggagtacg accgcaaggt     840
tgaaactcaa aggaattgac gggggcccgc acaagcggtg gagcatgtgg tttaattcga     900
agctacgcga agaaccttac caggtcttga catcttctgc caatcttaga gataagacgt     960
tcccttcggg gacagaatga caggtggtgc atggttgtcg tcagctcgtg tcgtgagatg    1020
ttgggttaag tcccgcaacg agcgcaaccc ttattatcag ttgccagcat tcagttgggc    1080
actctggtga gactgccggt gacaaaccgg aggaaggtgg ggatgacgtc aaatcatcat    1140
gccccttatg acctgggcta cacacgtgct acaatggacg gtacaacgag tcgcgaagtc    1200
gtgaggctaa gctaatctct taaagccgtt ctcagttcgg attgtaggct gcaactcgcc    1260
tacatgaagt tggaatcgct agtaatcgcg gatcagcatg ccgcggtgaa tacgttcccg    1320
ggccttgtac acaccgcccg tcacaccatg agagtttgta acacccaaa               1369
```

<210> SEQ ID NO 2

```
<211> LENGTH: 1272
<212> TYPE: DNA
<213> ORGANISM: Lactobacillus fermentum

<400> SEQUENCE: 2
aacagatgct aataccgcat aacagcgttg ttcgcatgaa caacgcttaa aagatggctt      60
ctcgctatca cttctggatg gacctgcggt gcattagctt gttggtgggg taacggccta     120
ccaaggcgat gatgcatagc cgagttgaga gactgatcgg ccacaatggg actgagacac     180
ggcccatact cctacgggag gcagcagtag ggaatcttcc acaatgggcg caagcctgat     240
ggagcaacac cgcgtgagtg aagaagggtt tcggctcgta aagctctgtt gttaaagaag     300
aacacgtatg agagtaactg ttcatacgtt gacggtattt aaccagaaag tcacggctaa     360
ctacgtgcca gcagccgcgg taatacgtag gtggcaagcg ttatccggat ttattgggcg     420
taaagagagt gcaggcggtt ttctaagtct gatgtgaaag ccttcggctt aaccggagaa     480
gtgcatcgga aactggataa cttgagtgca gaagagggta gtggaactcc atgtgtagcg     540
gtggaatgcg tagatatatg gaagaacacc agtggcgaag gcggctacct ggtctgcaac     600
tgacgctgag actcgaaagc atgggtagcg aacaggatta gataccctgg tagtccatgc     660
cgtaaacgat gagtgctagg tgttggaggg tttccgccct tcagtgccgg agctaacgca     720
ttaagcactc cgcctgggga gtacgaccgc aaggttgaaa ctcaaaggaa ttgacggggg     780
cccgcacaag cggtggagca tgtggtttaa ttcgaagcta cgcgaagaac cttaccaggt     840
cttgacatct tgcgccaacc ctagagatag ggcgtttcct tcgggaacgc aatgacaggt     900
ggtgcatggt cgtcgtcagc tcgtgtcgtg agatgttggg ttaagtcccg caacgagcgc     960
aacccttgtt actagttgcc agcattaagt tgggcactct agtgagactg ccggtgacaa    1020
accggaggaa ggtggggacg acgtcagatc atcatgcccc ttatgacctg gctacacac    1080 gtgctacaat ggacggtaca acgagtcgcg aactcgcgag ggcaagcaaa tctcttaaaa    1140
ccgttctcag ttcggactgc aggctgcaac tcgcctgcac gaagtcggaa tcgctagtaa    1200
tcgcggatca gcatgccgcg gtgaatacgt tcccgggcct tgtacacacc gcccgtcaca    1260
ccatgagagt tt                                                       1272

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
agagtttgat cmtggctcag                                                 20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
ggttaccttg ttacgactt                                                  19

<210> SEQ ID NO 5
<211> LENGTH: 24
<212> TYPE: DNA
<213> ORGANISM: Artificial Sequence
```

```
<220> FEATURE:
<223> OTHER INFORMATION: primer

<400> SEQUENCE: 5
cttatgcagg gatttgtggg actg                                              24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
cttgttccag actaacttcg tggc                                              24

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
ggtgctaaga acattacccg ttgg                                              24

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ccaagtccgt aatgagaacc cttc                                              24

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
gatcaatacc ccatctgcta tcgg                                              24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gtgggtactt cacgtgagtc ttag                                              24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
gaaaatctgt gttcccactc gctg                                              24
```

-continued

```
<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
ggtggtcctg gtaatttaag ctgg                                              24

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gggcaagtat gtacttcctc caag                                              24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
cttaattcac gaccgtaacc ggag                                              24

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
ctactctccg gtgaaaagct gag                                               23

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
cttgatccct ggcatatcct tgag                                              24
```

MICROORGANISM HAVING ABILITY TO DEGRADE ETHANOL AND ACETALDEHYDE, AND COMPOSITION AND KIT EACH INCLUDING THE SAME

CROSS-REFERENCE TO RELATED APPLICATION

This application claims the benefit of Korean Patent Application No. 10-2017-0184821, filed on Dec. 29, 2017, in the Korean Intellectual Property Office, the disclosure of which is incorporated herein in its entirety by reference.

REFERENCE TO SEQUENCE LISTING SUBMITTED ELECTRONICALLY

The content of the electronically submitted sequence listing in ST25 file (Name: Sequence Listing.txt; Size: 6.720 KB; and Date of Creation: Oct. 8, 2018) filed with the application is incorporated herein by reference in its entirety.

BACKGROUND

1. Field

The present disclosure relates to a microorganism having an ability to degrade ethanol and acetaldehyde, and a composition and a kit each including the microorganism.

2. Description of the Related Art

*Lactobacillus* is a genus of Gram-positive, facultative anaerobic or microaerophilic, rod-shaped, non-spore-forming bacteria. In addition, *Lactobacillus* is a major part of the lactic acid bacteria (LAB) group.

After ingestion, alcohol is easily absorbed by diffusive action in the upper part of the stomach and small intestine. Alcohol metabolism occurs mainly in liver tissue. In this regard, alcohol is oxidized to acetaldehyde by alcohol dehydrogenase (ADH), and acetaldehyde is converted to acetic acid by aldehyde dehydrogenase (ALDH).

Acetaldehyde is a metabolite produced by oxidation of alcohol, and is a highly reactive toxic substance. Acetaldehyde covalently binds to a variety of proteins in the liver, thereby altering liver function and structure. Through its binding to tubulin, acetaldehyde decreases polymerization of microtubules, thereby impairing protein secretion and causing swelling of hepatocytes. Acetaldehyde adduct formation also impairs some enzyme activity. Either directly or through binding with GSH, acetaldehyde promotes lipid peroxidation. Further, acetaldehyde alters various mitochondrial functions, particularly after chronic ethanol consumption which sensitizes mitochondria to the toxic effects of acetaldehyde. In cultured myofibroblasts, acetaldehyde stimulates collagen production, which is reported to be a cause of liver fibrosis in chronic alcoholics. Additionally, chronic alcohol consumption may lead to fatty liver, alcoholic hepatitis, cirrhosis, etc. The acetaldehyde-protein adducts stimulate production of antibodies against acetaldehyde epitopes. This immune response may contribute to aggravation or perpetuation of alcohol-induced liver damage. Acetaldehyde also causes hangovers.

Even according to the above-mentioned prior art, there is a demand for bacteria of the genus *Lactobacillus* having alcohol and acetaldehyde degradation activity.

SUMMARY

An aspect provides a microorganism having an ability to degrade ethanol and acetaldehyde, the microorganism being selected from the group consisting of *Lactobacillus brevis* LMT1-73 (Accession No. KCTC-13412BP) and *Lactobacillus fermentum* LMT2-75 (Accession No. KCTC-13413BP).

Another aspect provides a composition including the microorganism or a lysate thereof.

Still another aspect provides a kit which is used to remove one or more of ethanol and acetaldehyde from a sample, the kit including the microorganism and a diluent or carrier.

BRIEF DESCRIPTION OF THE DRAWINGS

These and/or other aspects will become apparent and more readily appreciated from the following description of the embodiments, taken in conjunction with the accompanying drawings in which:

FIG. 1 shows mucoadhesion of selected strains to intestinal epithelial cells.

DETAILED DESCRIPTION

An aspect provides a microorganism having an ability to degrade ethanol and acetaldehyde, the microorganism being selected from the group consisting of *Lactobacillus brevis* LMT1-73 (Accession No. KCTC-13412BP) and *Lactobacillus fermentum* LMT2-75 (Accession No. KCTC-13413BP).

The microorganism has excellent ethanol resistance and an excellent ability to degrade ethanol and/or acetaldehyde, and also has excellent acid resistance, bile acid resistance, and intestinal mucoadhesion. The microorganism was isolated from kimchi.

Another aspect provides a composition including the microorganism or a lysate thereof.

The composition may include a diluent or carrier acceptable for use in foods. The diluent may be water, a medium, or a buffer such as PBS. The carrier may be a common excipient, disintegrant, binder, lubricant, thickener, or filler. The diluent or carrier may be lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, or mineral oil. Further, the composition may include a lubricant such as magnesium stearate or talc.

The composition may be used to remove one or more of ethanol and acetaldehyde from a sample. The term "remove" means that concentrations of one or more of ethanol and acetaldehyde in a sample are reduced, including the complete removal. The sample may be a body fluid. The sample may be an intestinal fluid or blood. The intestinal fluid may be gastric juice, duodenal juice, small intestinal fluid, or large intestinal fluid.

The composition may be a formulation for oral administration. The composition may be a granule, a powder, a liquid, a tablet, a capsule, or a dry syrup. The composition may be, for example, a culture obtained by culturing the microorganism in a medium, or a dry product thereof.

The composition may be a food. The food may be a dairy product, a food for preventing alcoholic liver diseases or relieving hangovers, or a food additive. The dairy product may be fermented milk, butter, cheese, or milk powder. The food may be a health functional food. The health functional food may be a health functional food for preventing alcoholic liver diseases or relieving hangovers. The food may also be beverages, confectionery, diet bars, chocolates, pizza, ramen, other noodles, gums, or ice creams.

The food may include a component commonly added during food preparation, for example, proteins, carbohydrates, fats, nutrients, seasonings, and flavors.

Carbohydrates used in food preparation may include sugars such as monosaccharides, for example, glucose, fructose, etc.; disaccharides, for example, maltose, sucrose, oligosaccharides, etc.; and polysaccharides, for example, dextrin, cyclodextrin, etc., and sugar alcohols such as xylitol, sorbitol, erythritol, etc. In addition, natural flavors and synthetic flavors such as saccharin and aspartame may be used as flavors. The natural flavors may be *stevia* extracts such as thaumatin, rebaudioside A, and glycyrrhizin.

The health functional food means a food that brings a specific effect on health when ingested.

In the composition, the microorganism may be included in an amount ranging from 0.01% by weight to 50% by weight, or 0.1% by weight to 20% by weight with respect to the weight of the composition. Further, the composition may include cells of 105 CFU/g to 1×109 CFU/g, or 1×105 CFU/g to 1×10$^8$ CFU/g based on the weight of the composition.

Another aspect provides a method of removing one or more of ethanol and acetaldehyde from a subject, the method including administering to the subject the microorganism having an ability to degrade ethanol and acetaldehyde, which is selected from the group consisting of *Lactobacillus brevis* LMT1-73 (Accession No. KCTC-13412BP) and *Lactobacillus fermentum* LMT2-75 (Accession No. KCTC-13413BP). The method may be used to prevent or treat a disease associated with accumulation of ethanol and/or acetaldehyde in the body. The disease may be alcoholic liver disease or hangovers. The subject may be a mammal. The mammal may be humans or mammals excluding humans.

Still another aspect provides a kit used to remove one or more of ethanol and acetaldehyde from a sample, the kit including the microorganism and a diluent or carrier. The kit may be provided separately from the microorganism and the diluent or carrier.

A microorganism according to an aspect, and a composition and a kit each including the microorganism may be used to remove one or more of ethanol and acetaldehyde from a sample.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein.

Accordingly, the embodiments are merely described below, by referring to the figures, to explain aspects of the present description. As used herein, the term "and/or" includes any and all combinations of one or more of the associated listed items.

Hereinafter, the present disclosure will be described in more detail with reference to Examples. However, these Examples are for illustrative purposes only, and the scope of the present disclosure is not intended to be limited by these Examples.

Example 1: Isolation and Identification of Microorganism Having Ability to Degrade Alcohol and Acetaldehyde In this example, microorganisms having an excellent ability to degrade alcohol and acetaldehyde were isolated from kimchi, and identified. As a result, it was found that the microorganisms had excellent ability to degrade alcohol and acetaldehyde in blood, acid resistance, bile acid resistance, and intestinal mucoadhesion to show excellent stability in the intestine.

1. Isolation and Identification of Strain (1) Isolation of Strain 20 g of kimchi directly prepared at home and stored at 4° C. was taken aseptically, and diluted in 180 ml of 0.85% NaCl solution, and homogenized using a stomacher for 5 minutes. The homogenized kimchi was serially diluted in a tube containing 9 ml of sterile 0.85% NaCl solution to prepare kimchi samples. Each of the kimchi samples were spread on MRS (Difco, USA) agar plate and incubated at 37° C. for 2 days to 3 days. The appeared colonies were classified according to their morphology and color, and purely isolated. Each of the isolated colonies was cultured in MRS liquid medium at pH 6.8 and 37° C. for 24 hours, and 230 kinds of colonies, of which culture medium had pH of 4.5 or less, were selected. The selected strains were tested for alcohol resistance, and alcohol and acetaldehyde degradation ability. Finally, two strains of *Lactobacillus brevis* LMT1-73 (Accession No. KCTC-13412BP) and *Lactobacillus fermentum* LMT2-75 (Accession No. KCTC-13413BP) having excellent alcohol and acetaldehyde degradation ability and intestinal stability were selected.

(2) In Vitro Test of Alcohol Resistance (2.1) Test of Alcohol Resistance 230 kinds of the isolated strains were cultured in media containing different concentrations of ethanol to examine alcohol resistance.

In detail, ethanol was added to MRS liquid medium at a concentration of 5%, 10%, 15%, or 20%, and final 10 ml of the media was used after being sterilized using a membrane filter. Each of 230 kinds of the activated strains was added to the MRS liquid medium at a density of 107 CFU/ml, followed by stationary culture at 37° C. Growth of the strains was examined by measuring absorbance at $OD_{600}$ nm. The measurement was performed before culture and at 4 hours after culture. Table 1 shows ethanol resistance of the selected two strains.

TABLE 1

| | | Alcohol concentration (v/v %) | | | |
|---|---|---|---|---|---|
| No. | Strain | 5 | 10 | 15 | 20 |
| 1 | LMT1-73 | +++ | +++ | ++ | ++ |
| 2 | LMT2-75 | +++ | +++ | +++ | +++ |

In Table 1, +, ++, and +++ represent 80% or more, 90% or more, and 100% cell growth, as compared with control groups which were cultured by adding ethanol and D.W in equal amounts, respectively.

As shown in Table 1, *Lactobacillus fermentum* LMT2-75 and *Lactobacillus brevis LMT*1-73 showed high growth even in MRS liquid media containing 20% alcohol.

(2.2) Comparison of Alcohol Resistance

Alcohol resistance of the two strains which were confirmed to have high alcohol resistance in (2.1) was compared with that of other species of strains. As comparative strains, *Lactobacillus brevis* KCTC3498$^T$ and *Lactobacillus fermentum* KCTC3112$^T$ which are type strains were used, and they are commercially available from KCTC.

The alcohol resistance test was performed in the same manner as in (2.1), except that comparative strains as shown in the following Table 2 were used. Table 2 shows results of comparing the alcohol resistance between strains.

TABLE 2

| No. | Species | Strain | Alcohol concentration (v/v %) | | | |
|---|---|---|---|---|---|---|
| | | | 5 | 10 | 15 | 20 |
| 1 | L. brevis | LMT1-73 | +++ | +++ | ++ | ++ |
| 2 | | KCTC3498$^T$ | ++ | + | + | ++ |
| 3 | L. fermentum | LMT2-75 | +++ | +++ | +++ | +++ |
| 4 | | KCTC3112$^T$ | ++ | ++ | + | + |

In Table 2, +, ++, and +++ are the same as in Table 1, and − represents no cell growth. As shown in Table 2, the two selected strains showed excellent alcohol resistance, as compared with the comparative strains of the same species.

(3) In Vitro Test of Alcohol and Acetaldehyde Degradation Ability (3.1) Test of Ethanol Degradation Ability Each of the two isolated strains, LMT1-73 and LMT2-75, was cultured in MRS liquid medium at 37° C. for 18 hours to obtain a culture at a cell density of 10⁹ CFU/3 ml. A 15 ml test tube containing 3 ml of the culture was prepared. Ethanol was added to the tube at a final concentration of 10 (v/v) %, and the tube was air-tightened with a cap, and left at 37° C. for 4 hours.

Next, the culture was centrifuged at 3000 rpm to remove cells, and a supernatant was taken. An alcohol concentration in the supernatant was measured. In detail, 100 μl of the supernatant and 6 mM NAD were mixed in 1.0 M Tris/HCl (pH 8.8) buffer at a final volume of 3 ml, and left at room temperature for 5 minutes. Absorbance at $OD_{340}$ nm was measured, and ($A_1$) alcohol dehydrogenase (ADH) (Sigma) was added and then absorbance at $OD_{340}$ nm was measured to determine ($A_2$) NADH consumption, which was converted into ethanol consumption. The ethanol consumption was calculated according to the following Equation. The results are shown in Table 3.

Ethanol consumption (%)=$\Delta A=(A_2-A_1)$sample−$(A_2-A_1)$blank

Ethanol retention (g/L)=$(0.7256/6.3)*\Delta A$

Ethanol consumption (%)=(Ethanol retention in sample/Ethanol retention in control)*100

TABLE 3

| No. | Strain | Ethanol consumption (%) |
|---|---|---|
| 1 | LMT1-73 | 97.9 |
| 2 | LMT2-75 | 98.6 |

As shown in Table 3, the two selected strains directly degraded about 98% of ethanol, indicating that these strains may be used in degrading alcohol in the intestine or body, and may relieve hangovers or may protect organs such as liver from alcohol.

(3.2) Test of Acetaldehyde Degradation Ability

Each of the two isolated strains, LMT1-73 and LMT2-75, was cultured in MRS liquid medium at 37° C. for 18 hours to obtain a culture at a cell density of 10⁹ CFU/2.7 ml. A 15 ml test tube containing 2.7 ml of the culture was prepared. Acetaldehyde was added to the tube at a final concentration of 0.01 M, and the tube was air-tightened with a cap, and left at 37° C. for 4 hours.

After completion of the reaction, the culture was filtered using a 0.2 μm membrane filter, and a cell-removed filtrate sample was used to measure acetaldehyde retention in the sample using an acetaldehyde detection kit (r-biopharm) in accordance with the manufacturer's instructions. Acetaldehyde consumption was calculated according to the following Equation. The results are shown in Table 4.

Acetaldehyde consumption (%)=$(A_2-A_1)$sample−$(A_2-A_1)$blank

Acetaldehyde retention (g/L)=$(0.7158/6.3)*\Delta A$

Acetaldehyde consumption (%)=(Acetaldehyde retention in sample/Acetaldehyde retention in control)*100

TABLE 4

| No. | Strain | Acetaldehyde consumption (%) |
|---|---|---|
| 1 | LMT1-73 | 98.2 |
| 2 | LMT2-75 | 95.0 |

As shown in Table 4, the two selected strains consumed 98.2% and 95.0% of acetaldehyde, respectively, indicating that these strains may decrease the concentration of acetaldehyde which is produced by alcohol oxidation and known as a major cause of hangovers, thereby reducing harmful symptoms that may occur in the body after alcohol ingestion.

(4) In Vivo Test of Alcohol and Acetaldehyde Degradation Ability

Rats were orally administered with alcohol and the selected strain to examine its effect on blood concentrations of alcohol and acetaldehyde. The rats were 5 to 6-week old male SD(Sprague Dawley) rats (weighing 140 g to 160 g) (Orient Bio, Inc., Seongnam, Korea).

The rats were preliminary raised with free access to solid feed and tap water for 1 week, and divided into a normal group, a control group, and an experimental group (three rats per group). The normal group indicates rats which were administered with PBS, the control group indicates rats which were administered with 40% EtOH, and Experimental group 1 and Experimental group 2 indicate rats which were administered with (Lactobacillus brevis LMT1-73 1×10⁸ CFU/rat/day+40% EtOH) and (Lactobacillus fermentum LMT2-75 1×10⁸ CFU/rat/day+40% EtOH), respectively.

After being preliminary raised and fasted for 18 hours, the experimental groups were administered once with the live strain of 1×10⁸ CFU/day per rat suspended in phosphate buffered saline (PBS, biosesang).

30 minutes later, the control group and the experimental groups were orally administered with 1.5 ml of 40 (v/v) % ethanol, and 5 hours later, 1.5 ml of blood was collected by cardiac blood collection. The collected blood was centrifuged at room temperature and 13,000 rpm for 10 minutes to separate blood plasma. Ethanol concentrations in the blood plasma were measured using an ethanol assay kit (Roche, USA). The results are shown in Table 5.

TABLE 5

| | Control group | Experimental group 1 | Experimental group 2 |
|---|---|---|---|
| Alcohol retention (%) | 100 | 24 | 79.3 |

As shown in Table 5, the amounts of alcohol detected in the blood plasma of the two experimental groups were lower than that of the control group.

Further, acetaldehyde concentrations in the blood plasma were measured using an assay kit of acetaldehyde which is an ethanol degradation product (Roche, USA).

The results are shown in Table 6.

TABLE 6

|  | Control group | Experimental group 1 | Experimental group 2 |
|---|---|---|---|
| Acetaldehyde retention (%) | 100 | 4.4 | 47.6 |

As shown in Table 6, the amounts of acetaldehyde detected in the blood plasma of the two experimental groups were lower than that of the control group. Accordingly, it was confirmed that the strains may reduce alcohol and acetaldehyde concentrations in experimental animal models, thereby reducing harmful symptoms that may occur in the body after alcohol ingestion.

(5) Genetic Analysis of Selected Strains (5.1) 16S rDNA Analysis

PCR was performed using a primer set of SEQ ID NO: 3 and SEQ ID NO: 4, and genomes of the two isolated strains, LMT1-73 and LMT2-75 as a template to obtain 16S rDNA amplification products, respectively. Nucleotide sequences of the amplification products were confirmed by sequencing. As a result, 16S rDNAs of LMT1-73 and LMT2-75 have nucleotide sequences of SEQ ID NOS: 1 and 2, respectively.

Further, the nucleotide sequences of 16S rDNAs were analyzed using NCBI blast (http://www.ncbi.nlm.nih.gov/). As a result, 16S rDNAs of LMT1-73 and LMT2-75 had sequence homology of 99.9% and 100.0% to the species *Lactobacillus brevis* and *Lactobacillus fermentum*, respectively. Results of phylogenetic analysis also showed that LMT1-73 corresponds to the species *Lactobacillus brevis*, and LMT2-75 corresponds to the species *Lactobacillus fermentum*. Consequently, LMT1-73 and LMT2-75 strains were found to be novel strains belonging to the species of *Lactobacillus brevis* and *Lactobacillus fermentum*. These two strains were designated as *Lactobacillus brevis* LMT1-73 and *Lactobacillus fermentum* LMT2-75, respectively and deposited at the Korean Collection for Type Cultures (KCTC) of the Korea Research Institute of Bioscience and Biotechnology under accession number KCTC 13412BP and KCTC 13413BP on Dec. 5, 2017, respectively.

(5.2) Identification of Genes of Enzymes Associated with Alcohol and Acetaldehyde Degradation LMT1-73 and LMT2-75 were cultured in MRS liquid medium at 37° C. for 18 hours, respectively to recover cells. Genomic DNAs were obtained from the cells using a genomic DNA kit. PCR was performed using a primer set shown in Table 7 as primers and the genomic DNA as a template to confirm the presence of ADH, ALDH, and bifunctional acetaldehyde-CoA/alcohol dehydrogenase (ADHE) genes.

As a result, amplification products of ADH, ALDH, and ADHE genes were obtained from LMT1-73 and LMT2-75. These products were subjected to sequencing, and the obtained sequences were compared with other sequences using NCBI blast. As a result, ADH, ALDH, and ADHE genes of LMT1-73 corresponded to WP_011668736, WP_011668306, and WP_024855276, and ADH, ALDH, and ADHE genes of LMT2-75 corresponded to NZ_CP019030, CP002033.1 and NC_010610.1, respectively.

TABLE 7

| No. | Strain | Target gene | Primer (SEQ ID NO.) |
|---|---|---|---|
| 1 | LMT1-73 | *L. brevis* ADH | 5 |
|  |  |  | 6 |
| 2 |  | *L. brevis* ALDH | 7 |
|  |  |  | 8 |
| 3 |  | *L. brevis* ADHE | 9 |
|  |  |  | 10 |
| 4 | LMT2-75 | *L. fermentum* ADH | 11 |
|  |  |  | 12 |
| 5 |  | *L. fermentum* ALDH | 13 |
|  |  |  | 14 |
| 6 |  | *L. fermentum* ADHE | 15 |
|  |  |  | 16 |

(6) Morphological and Physiological Characterization of Selected Strains (6.1) Morphological Characterization The two selected LMT1-73 and LMT2-75 strains were spread on an MRS agar plate, respectively and cultured at 37° C. Morphologies of the colonies were examined. Table 8 shows morphological characteristics of LMT1-73 and LMT2-75.

TABLE 8

|  | LMT1-73 | LMT2-75 |
|---|---|---|
| Shape | Circular | Circular |
| Size | 2 mm | 1 mm |
| Color | Cream color | Cream color |
| Opacity | Opaque | Opaque |
| Elevation | Convex | Convex |
| Surface | Smooth | Smooth |
| Aerobic growth | + | + |
| Anaerobic growth | + | + |

(6.2) Sugar Fermentation Characteristics of Selected Strains

Sugar fermentation characteristics were examined using an API 50 CHL kit (Biomerieux, France) in accordance with the supplier's experimental guidelines. Table 9 shows sugar fermentation characteristics of LMT1-73 and LMT2-75.

TABLE 9

|  | LMT1-73 | LMT2-75 |
|---|---|---|
| Glycerol | − | − |
| Erythritol | − | − |
| D-arabinose | − | − |
| L-arabinose | + | + |
| D-ribose | + | + |
| D-xylose | + | − |
| L-xylose | − | − |
| D-adonitol | − | − |
| Methyl-β-D-xylopyranoside | − | − |
| D-galactose | + | + |
| D-glucose | + | + |
| D-fructose | + | + |
| D-mannose | − | + |
| L-sorbose | − | − |
| L-rhamnose | − | − |
| Dulcitol | − | − |
| Inositol | − | − |
| Mannitol | − | − |
| D-sorbitol | − | − |
| Methyl αD-mannopyranoside | − | − |
| Methyl αD-glucopyranoside | + | − |
| N-Acetyl Glucosamine | + | − |
| Amygdaline | − | − |
| Arbutin | − | − |
| Esculin | − | − |

TABLE 9-continued

|  | LMT1-73 | LMT2-75 |
| --- | --- | --- |
| Salicin | − | − |
| D-Cellobiose | − | + |
| D-maltose | + | + |
| D-lactose | − | − |
| D-melibiose | + | − |
| D-saccharose | − | − |
| D-trehalose | − | − |
| Inulin | − | − |
| D-melezitose | − | − |
| D-raffinose | − | − |
| Amidon | − | − |
| Glycogen | − | − |
| Xylitol | − | − |
| Gentiobiose | − | − |
| D-turanose | − | − |
| D-lyxose | − | − |
| D-Tagatose | − | − |
| D-fucose | − | − |
| L-fucose | − | − |
| D-arabitol | − | − |
| L-arabitol | − | − |
| Potassium gluconate | + | − |
| Potassium 2-ketogluconate | − | − |
| Potassium 5-ketogluconate | + | − |

(7) Intestinal Stability of Selected Strains (7.1) Examination of Acid Resistance The selected strains are required to pass through the stomach of low pH after ingestion to exert their probiotic efficacy in the intestine.

Each of the two selected strains was seeded in a sterile MRS liquid medium, and then cultured at 37° C. for 16 hours. Next, the selected strain was seeded at an amount of 1% in sterile MRS liquid medium of which pH was adjusted to pH 2.5 with HCl, and cultured at 37° C. for 2 hours. Immediately and 2 hours after seeding, the sample was recovered and diluted with a MRS liquid medium, and spread on an MRS agar plate, and cultured at 37° C. for 24 hours. Then, the number of colonies on the agar plate was counted to measure the number of cells. As a control group, the experiment was performed in the same manner, except that MRS (pH 6.8) liquid medium was used without pH adjustment, and the number of cells was counted. As comparative strains, Lactobacillus brevis KCTC3498$^T$ and Lactobacillus fermentum KCTC3112$^T$ which are type strains were used, and these strains are commercially available from KCTC. Table 10 shows results of measuring acid resistance.

TABLE 10

|  | Cell (CFU/ml) | | | |
| --- | --- | --- | --- | --- |
|  | LMT1-73 | LMT2-75 | KCTC3498$^T$ | KCTC3112$^T$ |
| MRS (pH 6.8) | 6.7 × 10$^9$ | 8.6 × 10$^9$ | 5.5 × 10$^9$ | 3.9 × 10$^9$ |
| MRS (pH 2.5) | 9.0 × 10$^8$ | 3.6 × 10$^9$ | 5.8 × 10$^8$ | 9.1 × 10$^6$ |

As shown in Table 10, the selected strains had excellent resistance against the acid of pH 2.5, as compared with the comparative strains. Specifically, 13.4% and 41.2% of the selected LMT1-73 and LMT2-75 were found to survive, respectively. In contrast, only 10.6% and 0.2% of Lactobacillus brevis KCTC3498$^T$ and Lactobacillus fermentum KCTC3112$^T$ which are comparative strains were found to survive, respectively. The selected strains showed characteristics of maintaining the proper number of cells at pH of lower than 3 close to the physiological pH of the stomach, indicating that the number of live cells may be stably maintained even at the low pH due to gastric juice and the cells may maintain a very high survival rate until they reach the intestine.

(7.2) Examination of Bile Acid Resistance

Each of the two selected strains was cultured in a medium containing bile acid to examine effects of bile acid on growth of the two strains.

In detail, each of the selected strains was seeded in a sterile MRS liquid medium, and then cultured at 37° C. for 24 hours. Each of the strains was seeded at an amount of 1% in MRS liquid medium containing 0.3% bile salts (Sigma, USA), considering that the concentration of bile salt in the intestine is about 0.1%, and cultured at 37° C. for 2 hours. Immediately and 2 hours after seeding, the sample was recovered and diluted with a MRS liquid medium, and spread on an MRS agar plate, and cultured at 37° C. for 24 hours. Then, the number of colonies on the agar plate was counted to measure the number of cells. As a control group, the experiment was performed in the same manner, except that MRS liquid medium without 0.3% bile salts was used, and the number of cells was counted. As comparative strains, Lactobacillus brevis KCTC3498$^T$ and Lactobacillus fermentum KCTC3112$^T$ which are type strains were used, and these strains are commercially available from KCTC. Table 11 shows results of measuring bile acid resistance.

TABLE 11

|  | Cell (CFU/ml) | | | |
| --- | --- | --- | --- | --- |
|  | LMT1-73 | LMT2-75 | KCTC3498$^T$ | KCTC3112$^T$ |
| MRS | 6.7 × 10$^9$ | 8.6 × 10$^9$ | 5.5 × 10$^9$ | 3.9 × 10$^9$ |
| MRS (0.3% bile salt) | 8.7 × 10$^8$ | 1.3 × 10$^8$ | 6.1 × 10$^8$ | 3.9 × 10$^7$ |

As shown in Table 11, the selected strains maintained the proper number of cells even at 0.3% bile salts higher than 0.1% which is similar to the actual concentration in the intestine. Specifically, 12.9% and 1.5% of the selected LMT1-73 and LMT2-75 strains were found to survive, respectively. In contrast, only 11.7% and 1.0% of Lactobacillus brevis KCTC3498$^T$ and Lactobacillus fermentum KCTC3112$^T$ which are comparative strains were found to survive, respectively. Accordingly, the selected LMT1-73 and LMT2-75 strains may survive well in the intestine of a human or an animal, and may maintain a very high survival rate until they reach the intestine.

(7.3) Examination of Intestinal Mucoadhesion

Each of the selected strains was co-cultured with Caco-2 intestinal epithelial cells, and the cell number of the selected strain that adhered to the epithelial cells was counted to examine mucoadhesion of the selected strain. Caco-2 cell which is a human epithelial colorectal adenocarcinoma cell was purchased from the Korean cell line bank (KCLB 30037.1).

In detail, Caco-2 cells were diluted at a density of 7×10$^4$ cells/100 μl using a cell culture medium, and added to each well of a 96-well culture plate, and cultured under conditions of 5% $CO_2$ and 37° C. to allow formation of a cell single layer. The used culture plate and medium were a 96-well cell culture plate (Corning, USA) and DMEM (Dulbecco's modified Eagle's medium) (Gibco, USA) supplemented with 10% fetal bovine serum (FBS) (Gibco, USA).

Next, LMT1-73 and LMT2-75 each cultured in MRS liquid medium were washed with phosphate buffered saline (PBS), and suspended in a DMEM medium without antibiotics, and added at a density of 1×107 CFU to the Caco-2 cell single layer, and cultured under conditions of 5% $CO_2$ and 37° C. for 2 hours. To remove cells that did not adhere to Caco-2 cells, the cells were washed with PBS five times, and the adhered cells were detached using 100 µl of 0.1% Triton x-100, spread on an MRS solid medium, and cultured at 37° C. for 24 hours. The number of colonies on the agar plate was counted to examine mucoadhesion of the selected strains.

FIG. 1 shows mucoadhesion of the selected strains to intestinal epithelial cells. As shown in FIG. 1, 73.7% and 72.9% of the selected LMT1-73 and LMT2-75 strains were found to adhere, respectively. In contrast, 68.0%, and 58.3% of *Lactobacillus brevis* KCTC3498$^T$ and *Lactobacillus fermentum* KCTC3112$^T$ which are comparative strains were found to adhere, respectively.

Accordingly, the selected *Lactobacillus brevis* LMT1-73 and *Lactobacillus fermentum* LMT2-75 strains showed excellent mucoadhesion to Caco-2 cells which are intestinal epithelial cells, as compared with the comparative strains.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the disclosure as defined by the following claims.

The invention claimed is:

1. A method for removing one or more of ethanol and acetaldehyde from a sample of a subject in need thereof, comprising administering a composition to the subject, wherein the composition comprises *Lactobacillus brevis* LMT1-73 (Accession No. KCTC-13412BP) and/or *Lactobacillus fermentum* LMT2-75 (Accession No. KCTC-13413BP), and a diluent or carrier.

2. The method of claim 1, wherein the sample is blood or is an intestinal fluid.

3. The method of claim 2, wherein the intestinal fluid is gastric juice, duodenal juice, small intestinal fluid, or large intestinal fluid.

4. The method of claim 1, wherein the composition is a food.

5. The method of claim 4, wherein the food is a dairy product, a food for preventing alcoholic liver diseases or relieving hangovers, or a food additive.

6. The method of claim 5, wherein the dairy product is fermented milk, butter, cheese, or milk powder.

7. The method of claim 1, wherein the composition is in the form of a liquid, a powder, granules, a tablet, or a capsule.

8. A method for removing one or more of ethanol and acetaldehyde from a sample of a subject in need thereof, comprising administering *Lactobacillus brevis* LMT1-73 (Accession No. KCTC-13412BP) and/or *Lactobacillus fermentum* LMT2-75 (Accession No. KCTC-13413BP) to the subject.

9. The method of claim 8, wherein the sample is blood or is an intestinal fluid.

10. The method of claim 9, wherein the intestinal fluid is gastric juice, duodenal juice, small intestinal fluid, or large intestinal fluid.

* * * * *